United States Patent
Wagner et al.

(10) Patent No.: US 7,491,191 B2
(45) Date of Patent: Feb. 17, 2009

(54) KEEP VEIN OPEN METHOD AND INJECTOR WITH KEEP VEIN OPEN FUNCTION

(75) Inventors: Gary S. Wagner, Independence, KY (US); Frank Fago, Mason, OH (US)

(73) Assignee: Liebel-Flarsheim Company, Cincinnati, OH (US)

( * ) Notice: Subject to any disclaimer, the term of this patent is extended or adjusted under 35 U.S.C. 154(b) by 734 days.

(21) Appl. No.: 10/779,285

(22) Filed: Feb. 13, 2004

(65) Prior Publication Data

US 2005/0182371 A1    Aug. 18, 2005

(51) Int. Cl.
*A61M 37/00*    (2006.01)
*A61M 5/315*    (2006.01)
*A61M 5/00*    (2006.01)

(52) U.S. Cl. .................. 604/228; 604/235; 604/6.11

(58) Field of Classification Search ............. 604/6.11, 604/6.12, 65–67, 118, 119, 121, 218, 228, 604/235, 230, 223; 128/DIG. 1, DIG. 12, 128/DIG. 13

See application file for complete search history.

(56) References Cited

U.S. PATENT DOCUMENTS

| | | | |
|---|---|---|---|
| 3,834,387 A | 9/1974 | Brown | 128/218 |
| 4,006,736 A | 2/1977 | Kranys et al. | 128/2 A |
| 5,188,603 A | 2/1993 | Vaillancourt | 604/131 |
| 5,207,642 A | 5/1993 | Orkin et al. | 604/65 |
| 5,249,579 A | 10/1993 | Hobbs et al. | 128/662.02 |
| 5,304,126 A | 4/1994 | Epstein et al. | 604/67 |
| 5,314,415 A | 5/1994 | Liebert et al. | 604/218 |
| 5,346,470 A | 9/1994 | Hobbs et al. | 604/24 |
| 5,472,403 A | 12/1995 | Cornacchia et al. | 600/4 |
| 5,782,805 A | 7/1998 | Meinzer et al. | 604/131 |
| 5,800,397 A | 9/1998 | Wilson et al. | 604/151 |

(Continued)

FOREIGN PATENT DOCUMENTS

EP    0192786    9/1986

(Continued)

OTHER PUBLICATIONS

Mallinckrodt, *Optistar LE Power Injector*, Mallinckrodt Imaging—Product Detail—Optistar LE Power Injector.

(Continued)

*Primary Examiner*—Matthew F Desanto
(74) *Attorney, Agent, or Firm*—Wood, Herron & Evans, LLP

(57) ABSTRACT

The present invention embodies a method and an injector adapted to incorporate this method, for keeping a patient's vein open during an intravenous contrast injector procedure without injecting a saline solution from a separate syringe. The injector includes a controller having a programable software module to allow an operator to configure the injector to push some contrast media fluid through an injection site and then retract a plunger drive ram. A syringe is adapted to allow a patient's blood pressure to move the syringe plunger back towards its starting position, thus enabling a patient's blood to pass through the injection site. Alternatively, the syringe is adapted with an elastic plunger which as it enlarges and contracts facilitates fluid communication through the injection site. Additionally, the plunger drive ram can be adapted to gradually pull as well as push the plunger, thereby causing fluid to flow across the injection site.

3 Claims, 4 Drawing Sheets

U.S. PATENT DOCUMENTS

| | | |
|---|---|---|
| 5,806,519 A | 9/1998 | Evans, III et al. ............ 128/654 |
| 5,808,203 A * | 9/1998 | Nolan et al. ................... 73/700 |
| 5,868,710 A | 2/1999 | Battiato et al. ............... 604/123 |
| 5,947,935 A * | 9/1999 | Rhinehart et al. ............ 604/218 |
| 6,200,289 B1 * | 3/2001 | Hochman et al. .............. 604/67 |
| 6,230,040 B1 | 5/2001 | Wang et al. ................... 600/415 |
| 6,339,718 B1 | 1/2002 | Zatezalo et al. .............. 600/432 |
| 6,432,089 B1 * | 8/2002 | Kakimi et al. ............... 604/218 |
| 2002/0007116 A1 | 1/2002 | Zatezalo et al. .............. 600/432 |
| 2002/0165491 A1 * | 11/2002 | Reilly ......................... 604/154 |
| 2003/0216643 A1 | 11/2003 | Zatezalo et al. .............. 600/432 |
| 2004/0158205 A1 * | 8/2004 | Savage ....................... 604/151 |

FOREIGN PATENT DOCUMENTS

| | | |
|---|---|---|
| EP | 1166807 | 1/2002 |
| EP | 1362606 | 11/2003 |

OTHER PUBLICATIONS

PCT/US2005/004348 International Search Report.

* cited by examiner

KEEP VEIN OPEN METHOD AND INJECTOR WITH KEEP VEIN OPEN FUNCTION

FIELD OF THE INVENTION

The present invention relates to injectors for injecting fluid into patients.

BACKGROUND OF THE INVENTION

In a variety of medical procedures a fluid is injected into a patient for the purpose of diagnosis or treatment. For example, a contrast media fluid is injected into a patient to improve computed tomography (CT), angiographic, ultrasound, or magnetic resonance imaging (MRI) procedures. During such procedures, there are typically time periods where a contrast injector is connected to a patient, but procedural preparations delay the injection of the contrast media fluid. Since no fluid is flowing through the injection site during the delay, if the delay is long enough, blood at the injection site may begin to coagulate or clot. If a significant blood clot forms within the fluid path, the injection of contrast media fluid may be hindered.

One approach to keep the vein open before the main injection begins, is to slowly drip the contrast media. However, this wastes contrast media, which, as used in MRI procedures, is very expensive. To prevent this premature and undesirable restriction or closure of the fluid path, without waste of contrast media, some injector systems include a second syringe, which is typically filed with a saline solution. During the time period when no contrast fluid is being injected, these injectors will intermittently dispense small bursts of saline into the fluid path.

There are, however, a number of problems associated with the use of a second syringe filled with saline. First, the addition of a second syringe can significantly increase the cost and complexity of the injector. Second, technologists are forced to set up two syringes with two different fluids, connecting Y-tubing instead of a single line tube, and must go through a more involved air purging process to rid both syringes and the Y-tubing of air. Y-tubing also is typically more expensive than a single line tube, thus also increasing the cost to the consumer. Finally, an imaging suite has to order and stock extra syringes for saline use and must dispose of additional medical waste after the saline syringes are used.

Accordingly, there is a need to simply and cost effectively keep a vein open during procedures without the use of a second syringe and a saline drip solution.

OBJECTS OF THE INVENTION

It is an object of the invention to keep the fluid path open during intravenous contrast injector procedures without injecting saline from a separate syringe. It is further an object of the invention to keep a fluid path open during imaging procedures in a simple and cost effective manner, and with a relatively simple and cost effective device.

SUMMARY OF THE INVENTION

The present invention provides a method for keeping a patient's vein open during an intravenous contrast injector procedure without the use or injection of a saline solution from a separate syringe. The present invention also provides and an injector adapted to incorporate this method. The injector includes a controller having a programable software module to allow an operator to configure the injector to push some contrast media fluid through an injection site and then retract a plunger drive ram. A syringe is adapted to allow a patient's blood pressure to push the syringe plunger back towards its starting position, thus enabling a patient's blood to pass back through the injection site.

Alternatively, the syringe is adapted with an elastic plunger which as it enlarges and contracts facilitates fluid communication through the injection site. Additionally, the plunger drive ram can be adapted to pull as well as push the plunger thereby causing fluid to gradually flow back and forth through the injection site. The cycle of advancing the plunger drive ram with a drive motor and allowing the syringe plunger to retract is repeatable, as needed, to discourage blood coagulation or clotting. Of significance, the present invention does not require the use of saline or a separate syringe containing a flush medium to keep the fluid path open.

The above and other objects and advantages of the present invention shall be made apparent from the accompanying drawings and the brief description thereof.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

DETAILED DESCRIPTION OF THE INVENTION

Figure 1:
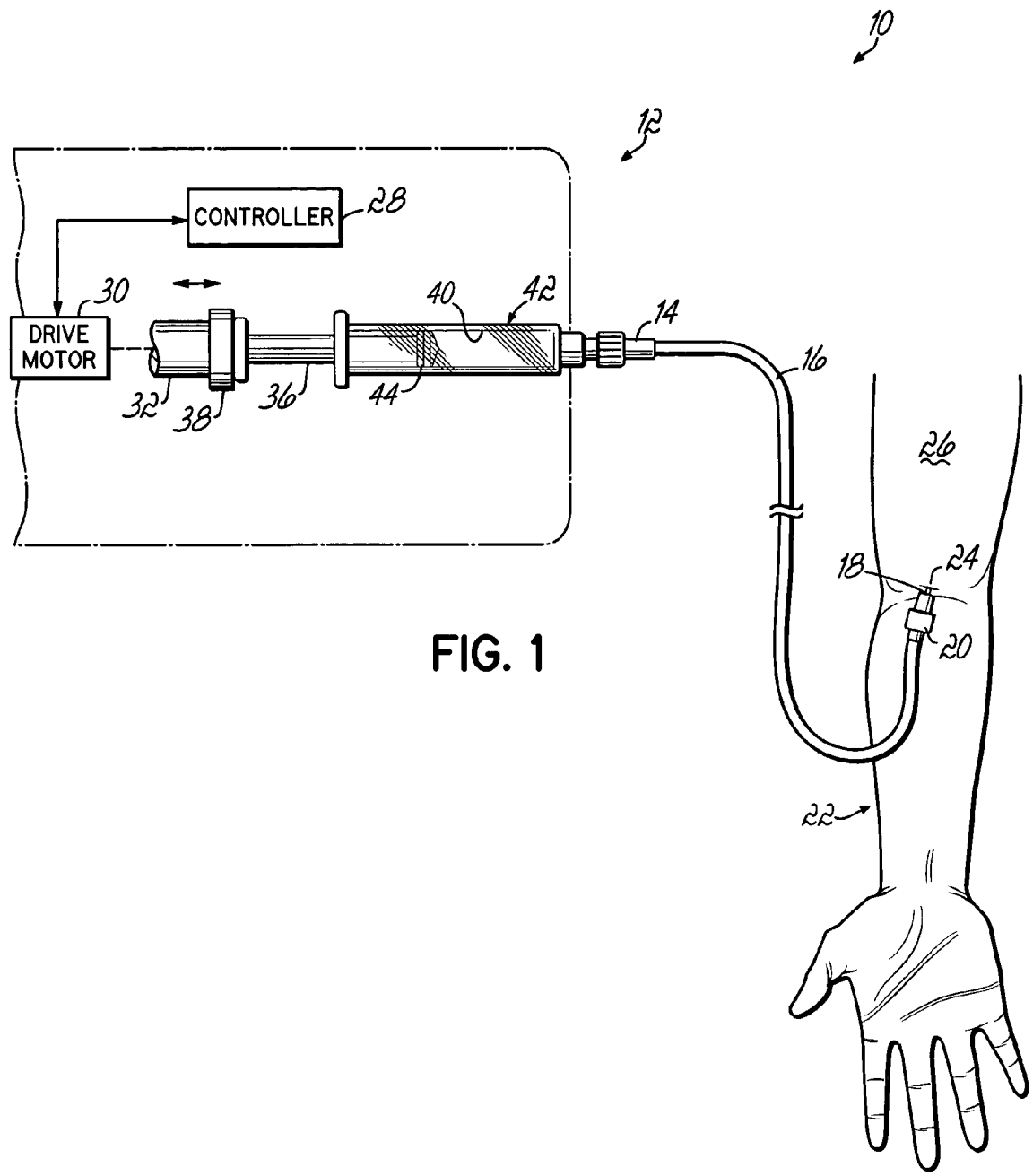
FIG. 1 is a partial environmental view of an injector for injecting fluids from a syringe into a patient in accordance with one embodiment of the present invention.

Referring to the Figures, and to FIG. 1 in particular, a Magnetic Resonance Imaging (MRI) system 10 is shown in accordance with the principles of the present invention although the invention is applicable to all other imaging and injector using environments. The MRI system 10 includes an MRI injector 12 which is attached via a connector 14 to a tube 16 which is in turn attached to a catheter 18 by another connector 20. The catheter 18 enters a patient 22 at an injection site 24. While FIG. 1 illustrates the injection site 24 on an arm 26 of a patient 22, the injection site 24 could also be located on other parts of a patient's anatomy. For example, in some MRI procedures, it may be desirable to locate the injection site 24 in a patient's groin area (not shown). Additionally, while FIG. 1 shows a portion of a human patient's anatomy, the MRI system 10 of the present invention could also be used on animal subjects. Finally, nothing prevents the present invention from being used for procedures other than MRIs. The present invention may be utilized whenever a fluid path into a blood vessel is desired to be kept open without the use of a second injection syringe.

The MRI injector 12 comprises a controller 28 which is operatively connected to a drive motor 30 which is used to mechanically advance or retract a plunger drive ram 32. The controller 28 and the drive motor 30 are typically electrically powered by AC current, but could also be battery powered or otherwise powered by DC current.

The controller 28 controls the cycles of advancing and retracting the plunger drive ram 32 via programmable software. Accordingly, an MRI technician may set the rate at which the plunger drive ram 32 is advanced, the amount of time the plunger drive ram 32 remains at its extended position, the rate at which it retracts, and the amount of time the plunger drive ram 32 remains at its retracted position before beginning the cycle again. The settings that the technician chooses may vary depending on the properties of the fluid 34 that is being injected, the physical characteristics of the patient 22, the size of the MRI injector 12, the size and length of the tubing 16, the estimated delay time before beginning the main injection, or any other like factors. Typically, the cycle of advancement and retraction will be repeated as needed until the MRI technologist starts the main contrast injection or terminates the cycle.

While the controller 28 may be preprogrammed to control the plunger drive ram 32 vis-a-vis the drive motor 30, the MRI technician may at anytime override the controller 28 or manually operate the MRI injector 12. Thus, while the plunger drive ram 32 will normally be advanced programmably as part of an injection procedure, the MRI technician may manually advance and retract the drive ram 32.

In addition to preprogramming or manually controlling the cycles of the plunger drive ram 32, the MRI system 10 may also incorporate pressure, fluid flow, or other like sensors and feedback control circuitry whereby the cycling of the plunger drive ram 32 is real time optimized based on the existing and possibly changing biological or mechanical conditions.

When the plunger drive ram 32 is advanced, it makes contact with and pushes the syringe plunger/pusher 36 forward within an interior fluid compartment 40 of a syringe 42. The fluid compartment 40 contains the fluid 34 that will be injected into the patient 22. As the syringe plunger/pushrod 36 is pushed forward, the head 44 of the syringe plunger/pushrod 36 pushes the fluid 34 forward and ultimately causes some fluid 34 to pass through the injection site 24 and into the patient 22. In MRI procedures, this fluid 34 is a contrast agent or a contrast medical fluid, however, any suitable medical fluid could be used for other procedures.

Figure 2A:
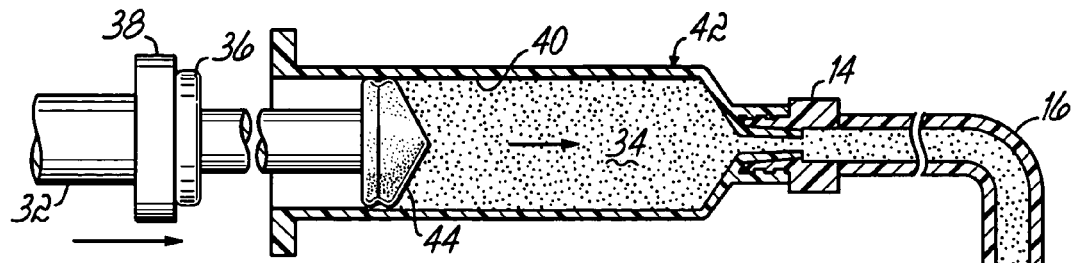
FIG. 2A is a diagrammatic partial cross-sectional view of the injector of FIG. 1 showing a syringe injecting fluid into a patient's blood stream.
Figure 2B:
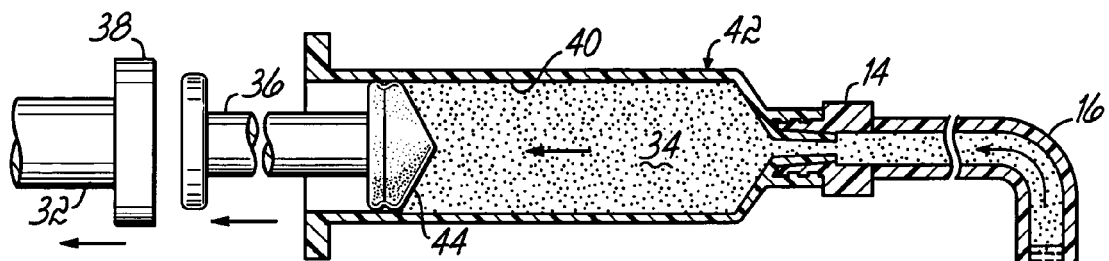
FIG. 2B is a diagrammatic partial cross-sectional view similar to FIG. 2A showing a patient's blood stream pressure pushing a syringe plunger back towards a drive ram.
Figure 2C:
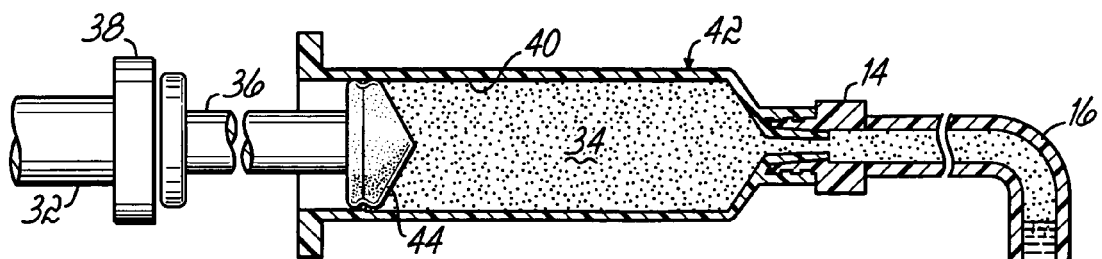
FIG. 2C is a diagrammatic partial cross-sectional view similar to FIGS. 2A and 2B showing the injector after the patient's blood pressure has returned the syringe plunger back to its general starting position at or near the position of the retracted drive ram.

FIGS. 2A, 2B and 2C further illustrate the process of the present invention which is performed by the injector in a keep vein open operative mode, or manually by the technician, before, after, or during a pause in a programmed injection procedure. This process involves sequential injection and withdrawal of fluid to/from the patient. Specifically, FIG. 2A shows the plunger drive ram 32 in contact with the syringe plunger/pushrod 36 and pushing the syringe plunger/pushrod 36 forward, whereby some amount of contrast agent 34 passes through the injection site 24 and into a patient's bloodstream 46. In the preferred embodiment, there is typically about 0.1 to 1 milliliter (mL) of contrast fluid 28 that is pushed through the injection site 24 by the syringe plunger/push rod 36. The pressure that is needed to inject fluid into the vein, while dependent on several factors, such as flow rate, tube length, and contrast agent 34 viscosity, will generally be less than 20 psi for typical applications. FIG. 2B shows the plunger drive ram 32 being retracted from contacting the syringe plunger/pushrod 36. As shown, once the plunger drive ram 38 is retracted, due to the patient's blood pressure, blood 48 from a patient's bloodstream 50 flows back through the injection site 24 and forces the fluid 34 to push the syringe plunger/pushrod 36 back towards the plunger drive ram 38. The contrast injector syringe 42 is adapted in a preferred embodiment to allow a patient 22 with a blood pressure of between about 50 to about 200 mm—Hg to move the syringe plunger/pushrod 36 back towards the plunger drive ram 32. Given a patient's blood pressure of about 50 to about 200 mm—Hg, the pressure pushing the contrast agent back through the catheter 18 is about 1 to about 4 psi. In this blood-pressure-return step, about 0.1 to 1 milliliter (mL) of a patient's blood 48, blood 48 mixed with other fluid 34, or even just the fluid 34, flows back through the injection site 24 due to the patient's own blood pressure.

FIG. 2C shows the end of the cycle when blood 48, from a patient's bloodstream 52, has flowed back towards the MRI injector 12 and caused the syringe plunger/pushrod 36 to move back to or near to its starting position which may be against or near the plunger drive ram 32. The injector then repeats the injection of a small amount of contrast and retraction of the ram as shown in FIGS. 2A and 2B. By repeating such cycles, flow is maintained in the catheter without substantial consumption of contrast media. It should be noted that the patient's blood pressure may not fully return the syringe plunger/pushrod to the initial position shown in FIG. 2A after a brief injection as shown in FIGS. 2B and 2C. In such a case, the subsequent brief injection of the desired amount of fluid may require advancement of the plunger by the injector during the second injection to a position that is more advanced than the position reached in the first injection. A pressure sensor on the injector may be advantageously used to determine whether and at what position the syringe plunger/pushrod 36 has engaged ram 32 as a consequence of the blood-pressure-return step. If an incomplete plunger return is achieved in the blood-pressure-return step, small amounts of contrast media may be consumed in the keep-vein-open procedure of the present invention, due to incomplete return of the plunger under influence of the patient's blood pressure, and a subsequent additional advance to inject the desired volume into the patient's vein. However, the amount of contrast media consumed in this manner will be substantially less than is the case in prior methods in which no blood-pressure-return step is implemented. The important point is not where the syringe plunger/pushrod 36 is finally pushed back to but rather simply that blood 48 or a blood 48 and other fluid 34 mixture or even pure fluid 34 flows back and forth through the area(s) likely to experience clotting problems, preventing clotting with reduced loss of contrast media.

Figure 3A:
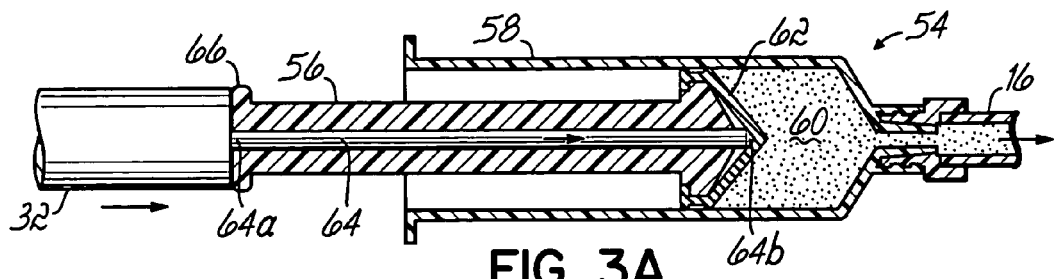
FIG. 3A is a diagrammatic partial cross-sectional view of an alternative embodiment of the injector of FIG. 1, showing a syringe injecting fluid into a patient's bloodstream.
Figure 3B:
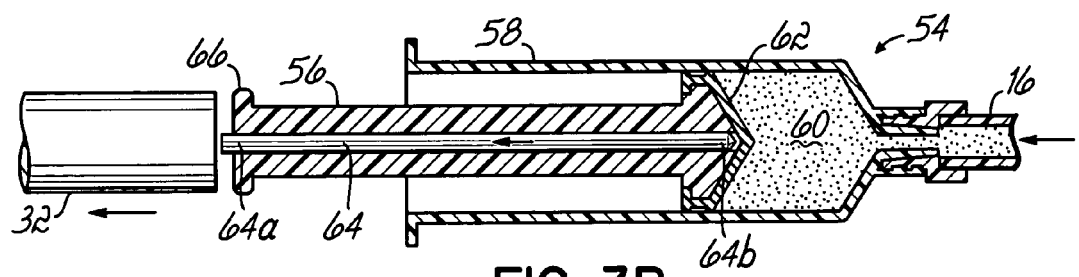
FIG. 3B is a diagrammatic partial cross-sectional view similar to FIG. 3A showing the elastic plunger in a contraptive state when the plunger drive ram is withdrawn.
Figure 3C:
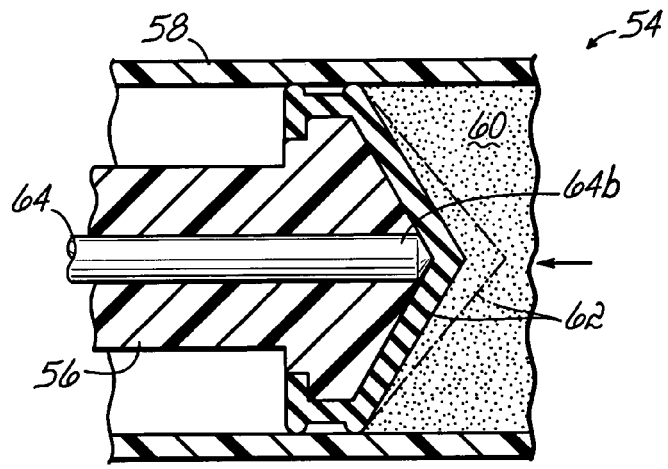
FIG. 3C is an enlarged view of a portion of FIG. 3B showing the plunger in its retracted state, and showing in phantom the position of the plunger in its extended state.

FIGS. 3A-3C show an alternative embodiment of the injector 54. FIG. 3A shows the injector 54 with the plunger/pushrod 56 in its extended position. This occurs when the plunger drive ram 32 advances or pushes against the plunger 56 and moves it forward in the barrel 58 of the syringe 54. As the plunger 56 advances, the volume of the fluid chamber 60 decreases.

The plunger 56 contains a plunger head 62 which pushes the fluid 34 into a tube 16 during the injection process. As shown, the head 62 is comprised of an elastic material, such as rubber, which allows it to elastically expand or advance and elastically contract or retract. The head 62 expands or stretches when the stretcher 64 pushes against it. The stretcher 64 can be a pin, a rod, a bar, a shaft, or the like. As shown in FIG. 3B, the end 64a of the stretcher 64 is proximally located to the drive ram 32 and is positioned so as to make contact with the drive ram before the drive ram contacts the flange 66 of the plunger 56. As the drive ram 32 moves forward, the pressure in the syringe 54 and the friction of the plunger 56 within the barrel 58 allows the distal end 64b of stretcher 64 to depress or enlarge or stretch the head 62 even before the plunger moves forward. Similarly, when the drive ram 32 is retracted, as shown in FIG. 3B, the head 62 elastically contracts or returns to its initial or relaxed starting position. Thus, as shown in FIG. 3C, the expansion and contraction of the head 62 adjusts the volume of the fluid chamber 60.

In operation, the drive ram 32 will advance the plunger 56 forcing fluid 34 through an injection site. During this push cycle, the stretcher 64 enlarges or expands the head 62. When the drive ram 32 is retracted, the head stretcher 64 also withdraws, allowing the head 62 to elastically relax and return to its original or contracted position. The return of the head 62 to its contracted position increases the volume of the fluid chamber 60 which draws fluid and/or blood back through the injection site. The drive ram 32 can continue to advance against the head structure 62 and withdraw, allowing the cycle of the expansion and contraction of the head 62 to continue as needed to facilitate fluid communication back and forth through the injection site. The volume of fluid displacement can be controlled and predetermined by the length of the stretcher 64.

Figure 4A:
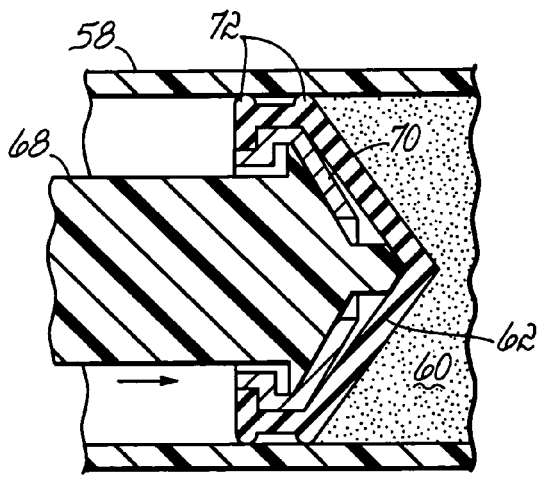
FIG. 4A is a cross-sectional view of an alternative embodiment of the injector shown in FIG. 3A showing the plunger in its extended position.
Figure 4B:
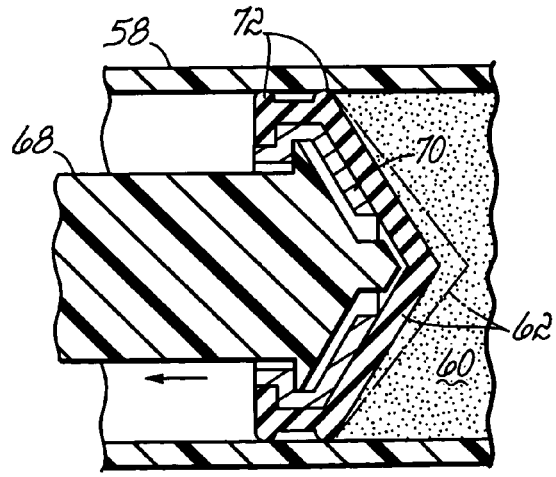
FIG. 4B is a cross-sectional view similar to FIG. 4A showing the elastic plunger in its retracted position.
Figure 5A:
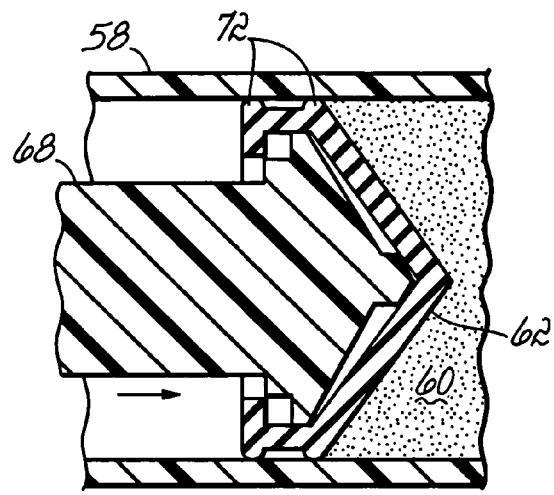
FIG. 5A is a cross-sectional view of an alternative embodiment of the injector shown in FIG. 4A showing the syringe plunger in its extended position.
Figure 5B:
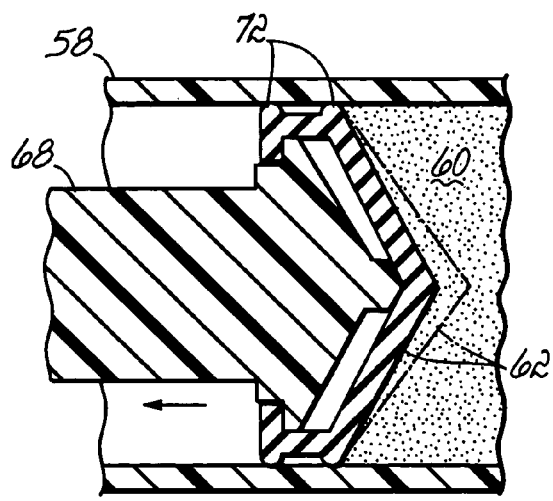
FIG. 5B is a cross-sectional view similar to FIG. 5A showing the plunger in its retracted position.

FIGS. 4A and 4B illustrate an alternative embodiment where the plunger 68 pushes against the head 62 to create the deformation or expansion of the head 62. As shown, a backer plate 70 is sandwiched between the head 62 and the plunger 68 and helps to maintain the integrity of the seals 72 that prevent the fluid 34 from leaking out of the barrel 58 of the injector 54. Here, as the plunger 68 advances, the head 62 is forced forward or away from the rigid backer plate 70. This movement as shown in FIG. 4B, decreases the volume of the fluid chamber 60. When the plunger is allowed to relax, the head 62 returns to its relaxed position against the rigid backer plate 70. This increases the volume of the fluid chamber 60 and draws a small amount of fluid and/or blood back through the injection site. FIGS. 5A and 5B show another alternative embodiment that operates as the embodiment shown in FIGS. 4A and 4B, but without a rigid backer plate 70.

Figure 6:
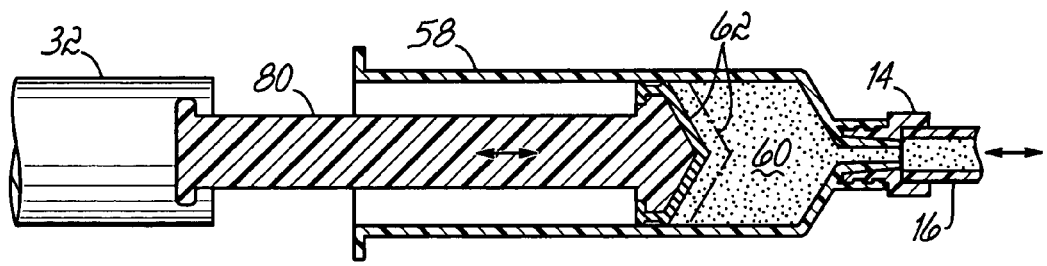
FIG. 6 is a diagrammatic partial cross-sectional view of an alternative embodiment of the injector shown in FIG. 1.

Another alternative embodiment of the present invention is shown in FIG. 6. In this embodiment, the plunger 80 is attached to the drive ram 32. A gripper or other like mechanism could be used to connect the plunger 80 with the drive ram 32. In this embodiment, the retraction or withdrawal of the drive ram 32 increases the volume of the fluid chamber 60 and draws a small amount of fluid and/or blood back through the injection site. The drive ram 32 can advance and retract as often as required, to push and pull blood and/or fluid through the catheter and the injection site.

In all of the embodiments of the present invention, the drawing of blood and/or fluid back through the injection site is done in such a way, as to not adversely extract oxygen out of the blood. Typically this means a gradual pulling of the blood. In addition, all the various seals and connectors of the system are secured and sealed so as to prevent oxygen from entering the system during the injection and/or withdrawal cycles. Finally, while the present invention has been illustrated with the initial cycle being the advancement of fluid into a catheter or through an injection site, the first cycle of the system could equally be the reception of blood and/or fluid through an injection site or a catheter.

While the present invention has been illustrated by description of various embodiments and while these embodiments have been described in considerable detail, it is not the intention of the applicants to restrict or in any way limit the scope of the claims to such detail. Additional advantages and modifications will readily appear to those skilled in the art. The invention in its broader aspect is, therefore, not limited to the specific details, representative system, apparatus, and method, and illustrative example shown and described. Accordingly, departures may be made from such details without departing from the spirit or scope of the applicant's general inventive concept.

What is claimed is:

1. An injector for injecting fluids from a syringe into a patient, the injector comprising:
    a plunger drive ram;
    a drive motor for moving the drive ram;
    a syringe for holding and injecting a fluid, the syringe having a plunger in operable contact with the drive ram,
    wherein the plunger has an elastic head distally positioned from the drive ram and a stretcher rod positioned between and in operable contact with the head and the drive ram, the head adapted to elastically expand as the drive ram advances against the stretcher rod and elastically contract as the drive ram retracts from the stretcher rod without sliding in the syringe; and
    a controller connected to the drive motor, the controller controlling the drive motor to advance and retract the drive ram.

2. The injector of claim 1, wherein the controller includes a programmable software module whereby an operator controls the advancement and retraction of the plunger drive ram.

3. The injector of claim 2, further comprising:
    a catheter operably connected to the syringe and connected to the patient at an injection site,
    wherein the software module is configured to cause the syringe to push between about 0.1 to about 1 milliliter of the fluid through the injection site.

* * * * *